(12) United States Patent
Brenner et al.

(10) Patent No.: US 6,224,589 B1
(45) Date of Patent: May 1, 2001

(54) LASER ADAPTER FOR MOUNTING ON A SURGICAL MICROSCOPE AND A LASER SUITABLE FOR THIS PURPOSE

(75) Inventors: Roland Brenner, Wallhausen; Martin Wiechmann, Aalen; Manfred Heymann, Heidenheim; Peter Reimer, Ellwangen; Theo Lasser, Oberkochen, all of (DE)

(73) Assignee: Carl-Zeiss-Stiftung, Heidenheim (DE)

(*) Notice: Subject to any disclaimer, the term of this patent is extended or adjusted under 35 U.S.C. 154(b) by 0 days.

(21) Appl. No.: 08/968,070

(22) Filed: Nov. 12, 1997

Related U.S. Application Data

(63) Continuation of application No. 08/490,742, filed on Jun. 15, 1995, now abandoned.

(30) Foreign Application Priority Data

Jun. 15, 1994 (DE) .................................. 44 20 734

(51) Int. Cl.[7] .................................. A61B 18/20
(52) U.S. Cl. .................. 606/10; 606/13; 606/17
(58) Field of Search .................. 606/2, 3–14, 17–19

(56) References Cited

U.S. PATENT DOCUMENTS

| 4,520,816 | 6/1985 | Schachar et al. |
| 4,692,924 | 9/1987 | Koizumi et al. |
| 4,702,245 | 10/1987 | Schröder et al. |
| 4,856,512 | 8/1989 | Lombardo et al. |
| 4,950,266 | * 8/1990 | Sinofsky ..................... 606/7 |
| 4,950,268 | * 8/1990 | Rink ........................... 606/12 |
| 5,057,100 | 10/1991 | Lombardo . |
| 5,067,951 | 11/1991 | Greve . |
| 5,092,865 | 3/1992 | Rink . |
| 5,153,426 | * 10/1992 | Konrad et al. ............... 606/11 |
| 5,219,347 | * 6/1993 | Negus et al. ................. 606/17 |
| 5,342,351 | 8/1994 | Blaha et al. . |

FOREIGN PATENT DOCUMENTS

WO 91/19539  12/1991  (WO).

\* cited by examiner

Primary Examiner—David M. Shay
(74) Attorney, Agent, or Firm—Walter Ottesen

(57) ABSTRACT

A laser adapter 2 for mounting on a surgical microscope 4 includes a compactly configured laser 9 which supplies a therapeutic laser beam 10 at a suitable wavelength. In addition, a pulse energy monitoring device is provided in the laser adapter 4 which is used for the on-line energy measurement of the emitted laser pulses and whose output signals are applied as parameters for controlling the pulse energy emitted by the laser 9.

14 Claims, 3 Drawing Sheets

LASER ADAPTER FOR MOUNTING ON A SURGICAL MICROSCOPE AND A LASER SUITABLE FOR THIS PURPOSE

This is a continuation of application Ser. No. 08/490,742, filed Jun. 15, 1995, now abandoned.

BACKGROUND OF THE INVENTION

In modern microsurgery, laser-surgical techniques are increasingly being utilized wherein lasers of different wavelengths are used in combination with a surgical microscope. Usually, these lasers are positioned at a certain distance from the surgical microscope and, depending on the wavelength used, articulated arms or fiber optic light guides are used for delivering the beam to the surgical site. In some surgical applications, lasers providing a medium output power are now adequate. These lasers can then be mounted directly on the surgical microscope in a suitable manner.

The positioning of a compact laser adapter directly on a surgical microscope is known from U.S. Pat. Nos. 5,057,100 and 4,856,512. The known laser adapter comprises a housing which is mounted below the surgical microscope. The laser itself is accommodated in an oblong and tiltable additional housing next to the housing of the laser adapter. The configuration of this device, in particular the laterally positioned additional housing including the $CO_2$ laser, is still relatively bulky, however, and can hamper the surgeon during surgery.

SUMMARY OF THE INVENTION

The object of the invention is to provide a laser adapter which is as simple and compact as possible. It is another object of the invention to provide such a laser which can be mounted on a surgical microscope. In addition, the laser should provide as much operational safety as possible in medical applications.

The laser pulse energy provided by the compactly configured laser in the laser adapter according to the invention is controlled by a pulse energy monitoring device in such a way that the pumping operation is interrupted when a defined, selectable energy per pulse has been reached. This makes it possible to implement the necessary cooling of the laser, for example, in the form of a relatively simple air or water cooling system. The overall result is a simple and compactly designed laser adapter according to the invention which can be mounted without difficulty below the surgical microscope and which, because of its small dimensions, does not hamper the surgeon.

In addition, the measures according to the invention guarantee high operational safety of the laser in medical applications. For example, the pulse energy monitoring device ensures that the pulses emitted by the laser do not exceed defined, selectable energy values.

A shutter is arranged in the therapeutic laser beam path and is coupled to the pulse energy monitoring device. The shutter can be swung into the beam path by an electric motor. This arrangement allows the shutter to be configured as a simple metal plate, that is, no complex wavelength-selective optical filter component is required. The arrangement according to the invention makes it possible to check the desired pulse energy of the laser by triggering one or several "trial shots" when the shutter is closed.

The use of the pulse energy monitoring device integrated in the laser according to the invention is not limited to the Er:YAG laser described in the following. In principle, a pulse energy monitoring device of this type can also be used in a different laser, resulting in the compact design required for the accommodation of the laser in a laser adapter of this type mounted on a surgical microscope.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
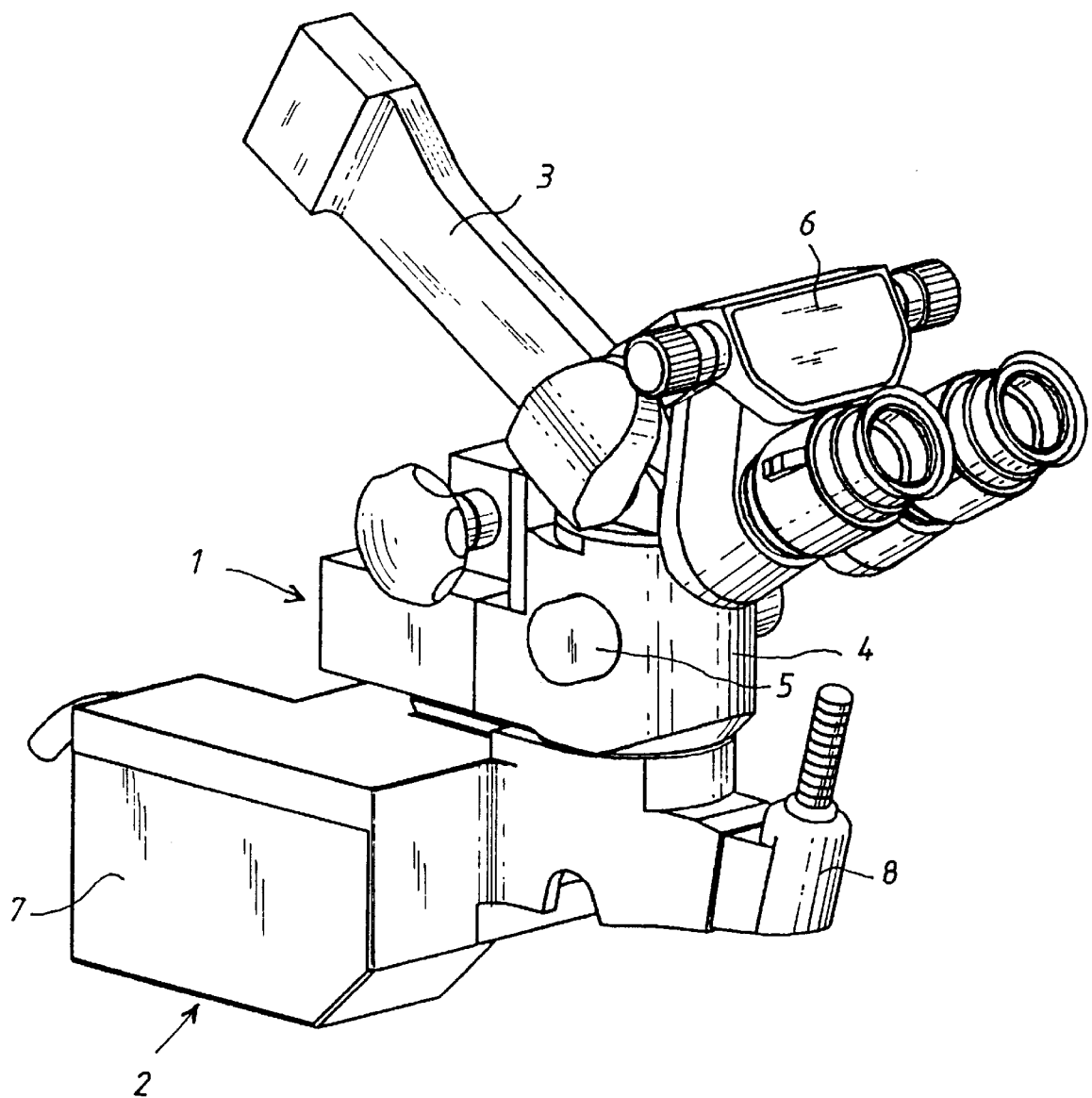
FIG. 1 is a perspective view of a surgical microscope in combination with the laser adapter according to the invention.

FIG. 1 shows a surgical microscope 1 combined with the laser adapter 2 according to the invention mounted thereon.

The surgical microscope 1 is flexibly connected via a connecting component 3 to a familiar floor stand or ceiling mount (not shown). The surgical microscope 1 to be used in combination with the laser adapter according to the invention is of a known configuration. For example, the surgical microscope body 4 includes a main objective lens (not shown) with a fixed or variable back focal distance and a downstream magnification changer system which can be set by the operator with knob 5 as required.

A familiar binocular tube 6 is provided on the top of the surgical microscope housing 4.

Below the surgical microscope body 4 the laser adapter according to the invention 2 is mounted such that it can be removed. To achieve this, a mechanical dovetail mount can be used. The rear part of the housing 7 of the laser adapter accommodates the individual components of the laser adapter according to the invention 2, while the front part of the housing 7 is provided with an opening for the main objective lens of the surgical microscope 1.

In addition, an operator-actuated element 8 of a mechanical micromanipulator is mounted on the housing 7 of the laser adapter and is shown in FIG. 1. The element 8 can be moved by the operator and is mechanically coupled to a deflection mirror accommodated in the adapter housing 7. This deflection mirror directs the therapeutic laser beam provided by the laser towards the surgical site as required. Micromanipulators suitable for this purpose are disclosed in U.S. Pat. No. 5,342,351 and in German utility model registration 9,408,098 published on Jul. 14, 1994.

Figure 2:
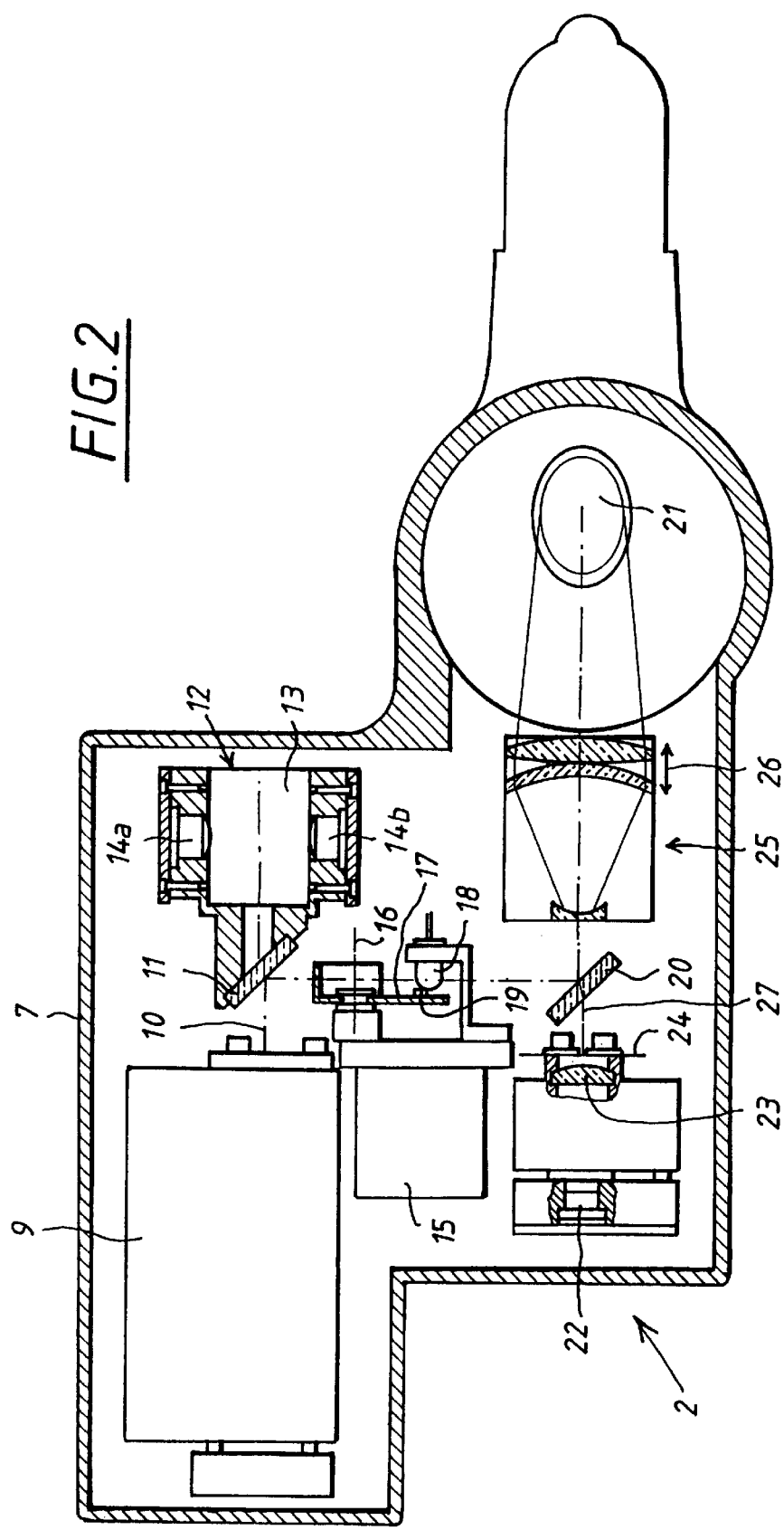
FIG. 2 shows the laser adapter according to the invention including individual components viewed from below; and, FIG. 3 is a block diagram of an embodiment of the laser according to the invention including the pulse energy monitoring device.

The basic configuration of the laser adapter according to the invention 2 is described in the following with reference to FIG. 2. FIG. 2 shows a view from below of the housing 7 of the laser adapter 2. The housing 7 of the laser adapter 2 accommodates a compactly configured laser 9. FIG. 2 only shows the outline of the optical cavity of this laser 9. In the embodiment shown, a solid-state laser of the Er:YAG type is used as the suitable laser which is optically pumped by a flashlamp. The flashlamp and the Er:YAG solid-state rod are accommodated in an elliptical cavity in a manner known per se. In addition, a suitable, highly reflecting mirror and a suitable partially transmitting coupling mirror are provided. The embodiment shown of the laser adapter according to the invention does not require any separate cooling, that is, especially no liquid cooling systems including pumps, etc.

This combination of a simple design and guaranteed high operational reliability is made possible by the measures taken according to the invention in combination with the laser 9 and described in more detail in the following.

If a higher pulse energy is required, it is relatively simple to implement liquid cooling of the cavity should that be necessary.

The Er:YAG laser used in the embodiment shown provides a therapeutic laser beam 10 at a wavelength of 2.94 $\mu$m. The pulse energies which can be attained using a laser 9 of this type lie in the range of 0–200 mJ at a pulse duration of 50–1000 $\mu$s.

In the laser adapter according to the invention 2, the laser beam 10 emitted by the laser 9 first falls on a first beam splitter 11. This beam splitter 11 couples out a portion of the therapeutic laser beam 10 and directs this portion to a pulse energy monitoring device. The portion coupled out of the therapeutic laser beam 10 lies in the range between 1% and 10% of the original total energy of the therapeutic laser beam 10. In the embodiment shown, the beam splitter component 11 is a plane-parallel plate which is arranged at 45° to the therapeutic laser beam. Other known physical beam splitter components such as cube beam splitters, prism beam splitters, possibly with necessary coatings, etc. can be used as alternatives. The portion of the therapeutic laser beam 10 coupled out then reaches a detector system 12 which is part of the pulse energy monitoring device.

The detector system 12 comprises a hollow chamber 13, the interior of which diffusely reflects the wavelength emitted by the therapeutic laser beam 10. Thus, the portion of the therapeutic laser beam 10 entering the chamber is multiply reflected, resulting in homogeneous illumination of the chamber 13. Two detectors (14a, 14b) are integrated in the walls of the chamber 13 to measure the energy of the laser pulses emitted. These detectors (14a, 14b) are configured as appropriately wavelength-selective photodiodes, for example, PbSe diodes or PbS diodes, pyroelectric detectors, Hg Cd Te-detectors or the like and operate independently of each other thereby ensuring a redundancy of the energy measurement. The homogeneous illumination of the chamber 13 ensures that the two detectors (14a, 14b) receive the same radiation intensity and, in the ideal case, supply identical signals to the CPU of the pulse energy monitoring device. Thus, a multichannel measurement of the laser pulse energy is obtained.

Figure 3:
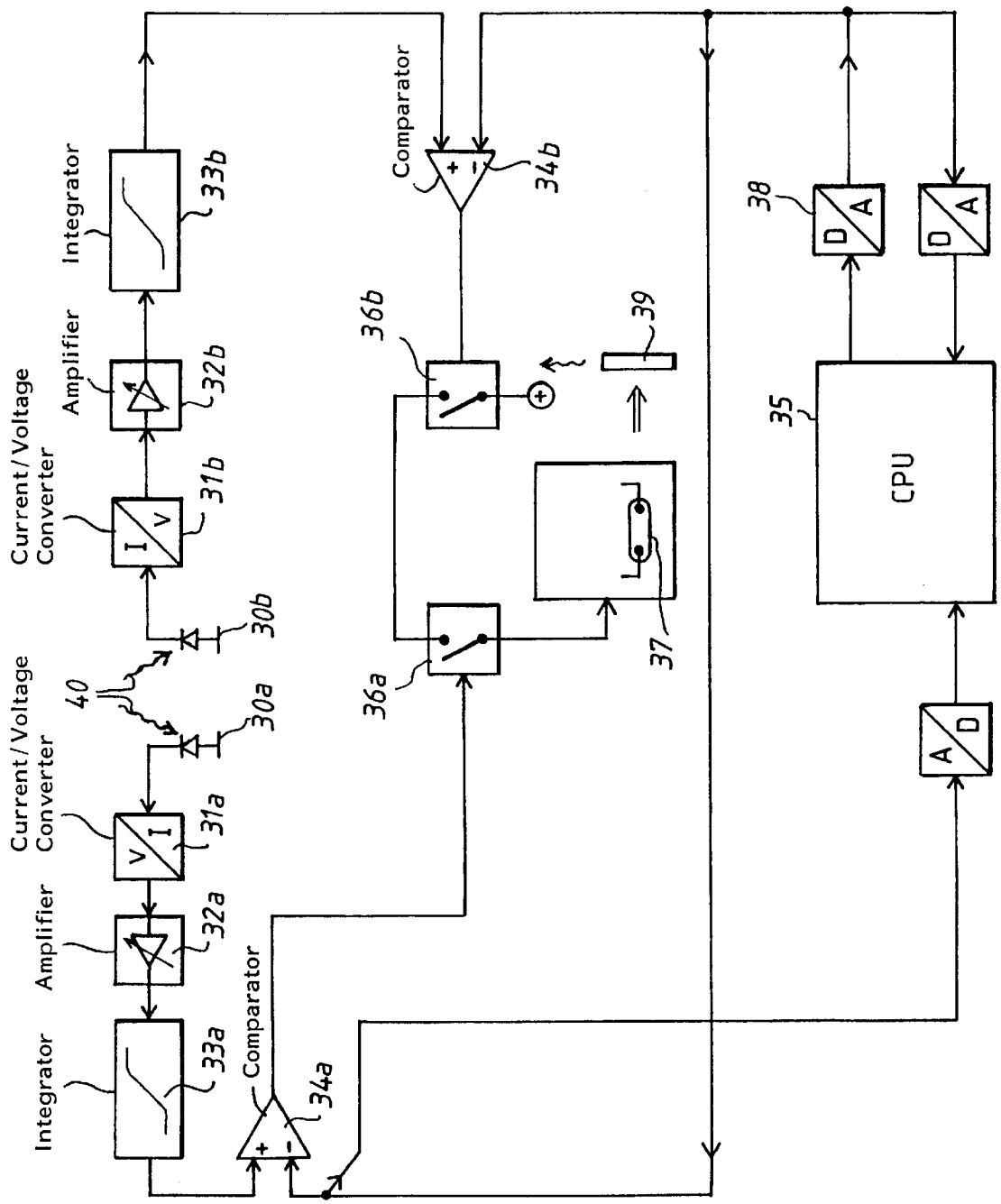

The description of FIG. 3 discusses the further signal processing taking place inside the pulse energy monitoring device of the laser according to the invention.

After being deflected by the first beam splitter 11, the portion of the therapeutic laser beam 10 not coupled out reaches a second beam splitter 20 after passing a motorized shutter 15 driven by an electric motor. This motorized shutter 15 comprises a shutter 17 rotatable about an axis 16 and configured as a simple angled plate. A suitable step motor is used as a drive motor. It is also possible, however, to use an attracting magnet operated by an electromotor, etc. Thus, the complete blocking or the passage of the therapeutic laser beam 10 is possible, depending on the rotational position of the shutter 17.

In addition, a monitoring device in the form of a light barrier is provided in the motorized shutter 15. The light barrier comprises a reflector 19 mounted on the shutter 17 and a phototransistor 18 located opposite the reflector. The monitoring device allows the monitoring of the position of the shutter 17, that is, depending on whether the phototransistor 18 detects a signal reflected from the reflector 19, it is possible, using a suitable evaluation circuit, to determine whether the shutter 17 blocks or passes the therapeutic laser beam 10.

In the laser adapter according to the invention, the positions of the beam splitter 11, the detector device 12, the pulse energy monitoring device and the motorized shutter 15 relative to each other now ensure that, when the shutter 17 is closed, a sequence of "test pulses" can be emitted by the laser and their energy can be determined by the pulse energy monitoring device. Thus, it is possible, without risk to the patient, to check as to whether the actual pulse energy corresponds to the desired pulse energy selected. Only after this has been ensured will the shutter 17 be opened and the therapeutic laser beam 10 released in the direction of the surgical site.

Another advantage of this relative positioning is that a simple thin plate can be used to block the therapeutic laser beam 10 at the location of the shutter, with the laser pulses impinging on the thin plate.

The second beam splitter 20 located in the therapeutic laser beam path 10 deflects the therapeutic laser beam 10 in the direction of the manipulator mirror 21. At the same time, however, the second beam splitter 20 coaxially unites the aiming laser beam 27 with the therapeutic laser beam 10. The aiming laser beam 27 lies in the visible spectral range and is produced by a laser diode 22. The laser diode 22 used produces light in the wavelength range of 630 to 680 nm at a power of 0.1 to 10 mW. One or several optical components 23 for expansion or dimensioning of the aiming laser beam 27 are mounted in front of the laser diode 22.

A diaphragm 24 is positioned in front of these optical components 23 in the aiming laser beam 27 and provides a specific reticle pattern in the target plane. For this purpose, any type of diaphragm, for example, a four-hole diaphragm can be selected which produces a number of light spots around the "invisible" therapeutic laser beam. This allows the surgeon to reliably assess the position of the therapeutic laser beam relative to the visible aiming laser beam.

In the beam path of the joined therapeutic laser beam and the aiming beam, the beam splitter 20 is followed by an optical zoom system 25 comprising several optical components. The zoom system 25 is used both for dimensioning the joined beams, in particular for beam expansion, and for focusing on the desired target plane. To achieve this, the zoom system 25 must be matched to the back focal distance of the main objective lens of the surgical microscope.

To allow beam dimensioning or beam focusing, at least one optical component of the zoom system 25 can be moved along the optical axis as indicated by the arrow 26. An actuating element (not shown) on the laser adapter allows the user not only to vary the cross section of the beam, but also to focus the beam as required by the specific application.

After traversing the zoom system 25, the joined laser beams impinge upon a movably-mounted manipulator mirror 21 which is mechanically connected to an actuating element (not shown in FIG. 2). This manipulator arrangement already mentioned allows the joined beams to be definitively positioned in the target plane.

The laser according to the invention and the pulse energy monitoring device used therewith will now be described with reference to FIG. 3 which shows a block diagram including important components of this arrangement.

A problem usually occurring when solid-state lasers are used is the formation of so-called thermal lenses due to the heating of the laser medium and the temperature gradient developing in the laser medium. For this reason, corresponding requirements on the cooling of the laser medium result. This situation is especially critical with Er:YAG lasers and other Er-doped or Cr-doped crystal materials such as YSGG. During the emission of several laser pulses, the crystal temperature changes during optical pumping, that is, heat builds up in the crystal. The output energy of the emitted laser pulses, however, is directly dependent on the temperature of the crystal. The heat buildup in the crystal is also dependent on the pulse frequency. As a result of these complex interrelationships, varying pulse energies and fluctuating pulse shapes are obtained during a series of pulses. In this case, both the pulse amplitudes and the pulse widths vary. Medical laser units, however, require as constant an output energy of the emitted laser pulses as possible.

According to the invention, the energy of the laser pulses emitted is therefore detected on line by the pulse energy monitoring device. As soon as a laser pulse displays the energy preselected by the user, the pumping operation is interrupted by one or several switching components of the pulse energy monitoring device. In the case of optical pumping this means that the pump current is switched off.

Hence, a constant energy per laser pulse is obtained, irrespective of the excitation conditions prevailing. This is a satisfactory solution to the problem described above, if the pulse powers or pulse frequencies used are not overly high, thereby allowing a compact laser configuration without the need for complex cooling systems.

An embodiment of a pulse energy monitoring device according to the invention in combination with an Er:YAG laser will now be described with reference to FIG. 3. Here, reference is again made to the dual channel energy measurement implemented in the embodiment of the laser adapter of FIG. 2, with a single channel energy measurement being adequate in principle.

The laser radiation of the therapeutic laser beam impinging upon the detectors (30a, 30b) is indicated by the arrows 40 and causes respective current pulses in the detectors (30a, 30b) which are configured as photodiodes. The voltage signals reach integrators (33a, 33b), respectively, via the current-voltage converters (31a, 31b) and the amplifiers (32a, 32b) in the two measuring channels. In the measuring channels, the integrators (33a, 33b) perform the summation of the registered instantaneous pulse power over the duration of a laser pulse. The integrator signals, that is the instantaneous energy of the laser pulses, then reach the corresponding inputs of respective comparators (34a, 34b) in the form of conventional, high-speed operational amplifiers.

An on-line comparison of the actual pulse energy with the selected desired energy is made in the comparators (34a, 34b). The desired input values of the pulse energy are transmitted by the CPU 35 of the pulse energy monitoring device via an appropriate digital-to-analog converter 38 to the other input of the comparator (34a, 34b). To allow the selection of the pulse energy, the CPU must be connected to a suitable input interface (not shown) which permits the user to enter the desired pulse energy for a particular application.

As soon as the comparator (34a, 34b) registers that the integrated measured pulse energy exceeds the desired input value, a signal is supplied to the switching element (36a, 36b). The particular switching element (36a, 36b) then directly interrupts the pumping operation of the laser medium 39 by the ignited flashlamp 37. This is achieved by switching off the discharge current of the flashlamp 37.

Almost at the same time that the pumping operation is interrupted, (that is, the discharge current of the flashlamp 37 is switched off) the laser activity in the excited laser medium 39 is interrupted. The result is a laser pulse with the pulse energy desired.

The embodiment shown in FIG. 3 is a multichannel pulse energy monitoring device. In principle, a device of this type can also be configured as a single channel design.

Attention is called to the fact that the principle of a pulse energy monitoring device of this type is not only suitable for use in an Er:YAG laser, but also in a wide variety of other laser types.

A possible application of the laser adapter according to the invention on a surgical microscope could be, for example, in microsurgery on the ear where relatively low laser powers suffice to perform the surgical procedures required. It is feasible, for example, to make defined openings in the eardrum using a laser adapter according to the invention and an integrated Er:YAG laser to ensure the necessary secretion drainage in middle ear infections. In addition, however, a wide variety of further applications can be implemented, especially in the areas of ENT, ophthalmology, etc.

It is understood that the foregoing description is that of the preferred embodiments of the invention and that various changes and modifications may be made thereto without departing from the spirit and scope of the invention as defined in the appended claims.

What is claimed is:

1. A compact pumped laser arrangement such as for mounting in a laser adapter on a surgical microscope, the pumped laser arrangement comprising:

a pumped laser for supplying radiation with a pumping operation for treating a patient, said radiation being emitted as laser pulses of actual pulse energy along a laser beam path;

a multichannel pulse energy monitoring device including: first and second detectors mounted downstream of said pumped laser, said first and second detectors being arranged for simultaneously detecting said radiation on line independently of each other; and, first and second measuring channels connected to respective ones of said first and second detectors to provide first and second signals, respectively, indicative of said actual pulse energy of said laser pulses;

a first beam splitter mounted on said laser beam path for coupling out a first portion of said radiation to provide outcoupled radiation and for directing a second portion of said radiation along a laser therapeutic beam path as a therapeutic laser beam;

said first and second detectors being mounted downstream of said pumped laser for receiving the outcoupled radiation;

said pulse energy monitoring device further including a housing having a hollow chamber receiving said outcoupled radiation therein;

said first and second detectors being mounted in said hollow chamber and said hollow chamber having an inner wall surface for diffusely reflecting said outcoupled radiation so as to ensure that said first and second detectors receive the same radiation intensity to measure said actual pulse energy of said laser pulses;

an adjusting device for providing a desired pulse energy signal indicative of a preselected desired pulse energy for treating the patient;

a switching apparatus including first and second switching elements connected to said first and second measuring channels, respectively, for receiving corresponding ones of said first and second signals and said first and second switching elements also being connected to said adjusting device for receiving said desired pulse energy signal; and, said first and second switching elements being operatively connected to said pumped laser for interrupting said pumping operation of said pumped laser to terminate said laser pulses when at least one of said first and second signals corresponds to said desired pulse energy signal.

2. The compact pumped laser arrangement of claim 1, said pumped laser being an Er:YAG laser.

3. The compact pumped laser arrangement of claim 1, said first and second detectors operating independently of each other.

4. The compact pumped laser arrangement of claim 1, said pumped laser including a solid-state laser and a flashlamp for optically pumping said solid-state laser.

5. The compact pumped laser arrangement of claim 4, said desired pulse energy signal of said adjusting device being a third signal; a first one of said measuring channels including: a first comparator for comparing said second and third signals and for emitting a first output signal when said second signal assumes a value corresponding to an energy of said laser pulses greater than said desired pulse energy; the second one of said measuring channels including a second comparator for comparing said first and third signals and for emitting a second output signal when said first signal assumes a value corresponding to an energy of said laser pulses greater than said desired pulse energy; and, said switching apparatus responding to either of said output signals to operate on said pumped laser to interrupt said pumping operation in said pumped laser.

6. The compact pumped laser arrangement of claim 1, further comprising: a control apparatus including said pulse energy monitoring device and a shutter located downstream of said first beam splitter; said shutter being movably mounted between a first position wherein said shutter is out of said therapeutic beam path and a second position wherein said shutter completely interrupts said therapeutic beam path; an electric drive for driving said shutter between said first and second positions in operative dependence upon said signal; and, position-monitoring means for monitoring said positions of said shutter.

7. The compact pumped laser arrangement of claim 6, further comprising an aiming laser for supplying an aiming laser beam in a visible spectral range; and, a second beam splitter mounted in said therapeutic beam path downstream of said shutter for coaxially uniting said aiming laser beam and said therapeutic laser beam.

8. The compact pumped laser arrangement of claim 6, said aiming laser including a laser diode mounted in said compact pumped laser for generating said aiming laser beam; and, optical means mounted forward of said laser diode for dimensioning and/or imparting a profile to said aiming laser beam.

9. The compact pumped laser arrangement of claim 8, further comprising zoom optic means mounted downstream of said second beam splitter for conjointly focussing and/or dimensioning said therapeutic laser beam and said aiming laser beam.

10. The compact pumped laser arrangement of claim 1, wherein said hollow chamber has an inlet opening formed therein for admitting said outcoupled radiation; and, said first and second detectors are mounted in said hollow chamber at substantially the same distance from said inlet opening.

11. A compact optically pumped laser arrangement such as for mounting in a laser adapter on a surgical microscope, the optically pumped laser arrangement comprising:

an optically pumped laser for supplying radiation with a pumping operation for treating a patient, said radiation being emitted as laser pulses of actual pulse energy along a laser beam path;

a device for supplying a desired value indicative of a desired value of pulse energy for treating the patient;

a multichannel pulse energy monitoring device including two detectors for detecting on-line said actual pulse energy of said laser pulses;

a first beam splitter mounted on said laser beam path for coupling out a first portion of said radiation to provide outcoupled radiation and for directing a second portion of said radiation along a laser therapeutic beam path as a therapeutic laser beam;

said first and second detectors being mounted downstream of said pumped laser for receiving the outcoupled radiation;

said pulse energy monitoring device further including a housing having a hollow chamber receiving said outcoupled radiation therein;

said first and second detectors being mounted in said hollow chamber and said hollow chamber having an inner wall surface for diffusely reflecting said outcoupled radiation so as to ensure that said first and second detectors receive the same radiation intensity to measure said actual pulse energy of said laser pulses;

said two detectors defining respective measuring channels for generating actual value signals indicative of said actual pulse energy of said laser pulses; first and second integrators mounted in said measuring channels, respectively, downstream of said detectors for determining respective instantaneous actual values of said actual pulse energy of said laser pulses; first and second comparators mounted downstream of said first and second integrators, respectively, for comparing said actual values to said desired value and for providing respective outputs when said instantaneous actual values exceed said desired value; and, first and second switching units connected into said measuring channels downstream of said comparators for switching off the pumping operation of said optically pumped laser in response to at least one of said outputs.

12. A method of treating a patient with a compact pumped laser which functions in a pulsed mode of operation, the method comprises the steps of:

exciting a pumped laser for supplying radiation emitted as laser pulses of actual pulse energy for treating a patient;

providing a multichannel energy monitoring device having two detectors for continuously detecting the actual pulse energy in the laser pulses of said laser;

a first beam splitter mounted on said laser beam path for coupling out a first portion of said radiation to provide outcoupled radiation and for directing a second portion of said radiation along a laser therapeutic beam path as a therapeutic laser beam;

said first and second detectors being mounted downstream of said pumped laser for receiving the outcoupled radiation;

said pulse energy monitoring device further including a housing having a hollow chamber receiving said outcoupled radiation therein;

said first and second detectors being mounted in said hollow chamber and said hollow chamber having an inner wall surface for diffusely reflecting said outcoupled radiation so as to ensure that said first and second detectors receive the same radiation intensity to measure said actual pulse energy of said laser pulses;

connecting two measuring channels to said detectors, respectively, to obtain respective signals indicative of said actual pulse energy of said laser pulses;

providing an adjusting device to provide a signal indicative of a preselected desired pulse energy for treating the patient;

comparing said signal indicative of a preselected desired pulse energy to said signals indicative of said actual pulse energy of said laser pulses; and, interrupting the pumping operation when said actual pulse energy reaches said preselected desired pulse energy.

13. A compact pumped laser arrangement such as for mounting in a laser adapter on a surgical microscope, the pumped laser arrangement comprising:

a main housing defining means for attaching said main housing to said surgical microscope;

a pumped laser for supplying radiation with a pumping operation for treating a patient and said pumped laser being mounted in said housing, said radiation being emitted as laser pulses of actual pulse energy along a laser beam path;

a two-channel pulse energy monitoring device mounted in said main housing and including: first and second detectors mounted downstream of said pumped laser, said first and second detectors being arranged for simultaneously detecting said radiation on line independently of each other; and, first and second measuring channels connected to respective ones of said first and second detectors to provide first and second signals, respectively, indicative of said actual pulse energy of said laser pulses;

a first beam splitter mounted on said laser beam path for coupling out a first portion of said radiation to provide outcoupled radiation and for directing a second portion of said radiation along a laser therapeutic beam path as a therapeutic laser beam;

said first and second detectors being mounted downstream of said pumped laser for receiving the outcoupled radiation;

said pulse energy monitoring device further including a detector housing having a hollow chamber receiving said outcoupled radiation therein;

said first and second detectors being mounted in said hollow chamber and said hollow chamber having an inner wall surface for diffusely reflecting said outcoupled radiation so as to ensure that said first and second detectors receive the same radiation intensity to measure said actual pulse energy of said laser pulses;

an adjusting device for providing a desired pulse energy signal indicative of a preselected desired pulse energy for treating the patient;

a switching apparatus including first and second switching elements connected to said first and second measuring channels, respectively, for receiving corresponding ones of said first and second signals and said first and second switching elements also being connected to said adjusting device for receiving said desired pulse energy signal;

said first and second switching elements being operatively connected to said pumped laser for interrupting said pumping operation of said pumped laser to terminate said laser pulses when at least one of said first and second signals corresponds to said desired pulse energy signal;

a control apparatus including said pulse energy monitoring device and a shutter located downstream of said first beam splitter;

said shutter being movably mounted between a first position wherein said shutter is out of said therapeutic beam path and a second position wherein said shutter completely interrupts said therapeutic beam path;

an aiming laser for supplying an aiming laser beam in a visible spectral range substantially parallel to said radiation emitted by said pumped laser;

said aiming laser being mounted in said main housing in spaced relationship to said pumped laser;

a second beam splitter mounted in said therapeutic beam path downstream of said shutter for coaxially uniting said aiming laser beam and said therapeutic laser beam substantially parallel to said radiation emitted by said pumped laser; and, a manipulator mirror also mounted in said main housing for deflecting said aiming laser beam and said therapeutic laser beam toward the surgical site.

14. The compact pumped laser arrangement of claim 13, further comprising zoom optic means for conjointly focussing and/or dimensioning said therapeutic laser beam and said aiming laser beam; and, said zoom optic means being mounted in said main housing between said second beam splitter and said manipulator mirror.

* * * * *